(12) United States Patent
Mizutani et al.

(10) Patent No.: US 7,806,881 B2
(45) Date of Patent: Oct. 5, 2010

(54) INTER-LABIAL PAD

(75) Inventors: Satoshi Mizutani, Kagawa (JP); Yuki Noda, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 258 days.

(21) Appl. No.: 11/149,958

(22) Filed: Jun. 10, 2005

(65) Prior Publication Data
US 2005/0277903 A1 Dec. 15, 2005

(30) Foreign Application Priority Data
Jun. 11, 2004 (JP) .............................. 2004-174865

(51) Int. Cl.
A61F 13/15 (2006.01)
A61F 13/20 (2006.01)

(52) U.S. Cl. ................................. 604/385.17
(58) Field of Classification Search ............ 604/385.17, 604/385.18
See application file for complete search history.

(56) References Cited

U.S. PATENT DOCUMENTS 6,254,584 B1    7/2001  Osborn, III et al.

FOREIGN PATENT DOCUMENTS

| EP | 1 426 025 A1 | 6/2004 |
|---|---|---|
| JP | 2001-507597 | 6/2001 |
| JP | 2001-507597 A | 6/2001 |
| JP | 2002-320638 A1 | 11/2002 |
| JP | 2004-097693 A1 | 4/2004 |
| JP | 2004-121611 A1 | 4/2004 |
| JP | 2004097693 A * | 4/2004 |
| WO | WO-98/29078 A1 | 7/1998 |
| WO | WO-02/094159 | 11/2002 |
| WO | WO-02/094159 A1 | 11/2002 |
| WO | WO-02/100315 A1 | 12/2002 |
| WO | WO-2004/024050 | 3/2004 |

OTHER PUBLICATIONS

English translation of JP 2004-097693.*

* cited by examiner

*Primary Examiner*—Melanie J Hand
(74) *Attorney, Agent, or Firm*—Morrison & Foerster LLP

(57) ABSTRACT

An inter-labial pad which can flexibly follow-up the fluctuation of pressure exerted on an inter-labial pad in the right-to-left direction caused to the inter-labial pad in a wearing state, in which an inter-labial pad is inserted between the labia of a wearer to be sandwiched by the labia, and the inter-labial pad comprises an absorbent body, the absorbent body is constituted with fibers capable of absorbing a menstrual blood, the direction of the fibers thereof is aligned in the direction along which an inter-labial pressure is caused in a wearing state and, accordingly, the inter-labial pad can be flexibly compressed and recovered, and can follow-up the inter-labial pressure in a wearing state to prevent leakage of menstrual blood or detachment of the inter-labial pad.

14 Claims, 7 Drawing Sheets

INTER-LABIAL PAD

CROSS-REFERENCE TO RELATED APPLICATIONS

This application is based upon and claims the benefit of priority from Japanese Patent application No. 2004-174865 filed on Jun. 11, 2004, the entire contents of which is incorporated herein by reference.

FIELD OF THE INVENTION

The present invention concerns an inter-labial pad a portion of which is put between female labia and abutted to the labial inner surface in wearing and, more specially, it relates to an inter-labial pad capable of flexibly following-up the fluctuation of pressure caused from the right-to-left direction of a wearer in the state of wearing.

RELATED ART

Heretofore, sanitary napkins and tampons have been used generally as women's sanitary articles. For the sanitary napkins, a great effort has been made in order to prevent leakage of menstrual blood from a gap caused by poor adhesion to the vicinity of an introitus. Further, also for the tampons, since due to their attribution they cause foreign-body sensation, uncomfortable feeling upon wearing and difficulty in insertion to the inside of a vagina, various devices have been made in order to avoid them.

Under the circumstances, sanitary articles referred to as inter-labial pads, which are of a hybrid type merging the features of the sanitary napkins and the tampons have become noted in recent years. The inter-labial pads are partially inserted between female labia and abutted against the inner surface of the labia in wearing. Accordingly, since the inter-labial pads have closer adhesion with a body compared with the sanitary napkins, leakage of the menstrual blood can be prevented and since they prevent the menstrual blood from diffusing and being in contact with a body at large area, they are sanitary and clean. Further, since the inter-labial pads are smaller in the size compared with the sanitary napkins, the inter-labial pads have a feature that they are excellent in the feeling of wearing and comfortable, and cause less psychological resistance compared with the tampons to be inserted inside of the vagina.

As inter-labial pads having such features, those of various structures have been developed. For example, patent document 1 mentioned bellow discloses an inter-labial pad which is folded at a fold line along the longitudinal center axis of the inter-labial pad such that a pair of portions of a back surface are opposed to each other in which the pair of portions of the back surface are joined in at least one joined portion with each other.

Further, as another example, commercial products having a liquid pervious surface side sheet, a liquid impervious back face sheet and an absorbent body interposed therebetween in which the back face sheet facing a garment is provided with a semi-circular gripping tag for attaching the inter-labial pad in an labia, and the tab is formed by embossing the back face sheet and the absorbent body simultaneously were sold trially in USA about from May, 2000 to May, 2001 (Envive: trade name of products, manufactured by Procter & Gamble Co.).

[Patent Document 1] International Publication Application laid-open No WO 02/100315 pamphlet Any of the inter-labial pads in the prior art described above is in a substantially longitudinal shape having a longitudinal direction and a lateral direction and it is inserted being folded along the longitudinal center line. In this case, when a pressure caused from the right and left sides of the labia to the inter-labial pad fluctuates, since a gap is formed between the labial inner wall and the inter-labial pad, it may be a risk of leakage or a possibility that the inter-labial pad detaches from the labia.

Particularly, in a moistened state where an absorbent body absorbs a body fluid, since fibers constituting the absorbent body are more tended to be slipped to each other, the inter-labial pad folded in two would not follow sufficiently to the fluctuation of the pressure in the right-to-left direction of a wearer in a state of wearing.

On the other hand, in the absorbent body constituted with fibers capable of absorbing a body fluid, fibers can be oriented into a predetermined direction by a manufacturing method or a post treatment. However, in conventional inter-labial pads, no consideration has been taken on the relation between the direction of arrangement of fibers constituting the absorbent body and the following-up property of the inter-labial pad with respect to the fluctuation of the pressure in the right-to-left directions caused to the inter-labial pad.

SUMMARY OF THE INVENTION

The present invention has been achieved in view of the problems as described above and intends to provide an inter-labial pad capable of flexibly follow-up the fluctuation of the pressure in the right-to-left direction caused to the inter-labial pad in the state of wearing.

More specifically, the invention provides an inter-labial pad comprising the following constitutions.

(1) An inter-labial pad having an absorbent body capable of absorbing a body fluid and being put between labia in wearing, comprising;
   a pressure following-up recoverable structure having predetermined compressibility and bulk recoverability responding to an inter-labial pressure caused to the inter-labial pad from the right and left sides of the labia in a state of wearing, wherein
   the pressure following-up recoverable structure is formed by orienting at least a portion of fibers constituting the inter-labial pad so as to direct in the right-to-left direction of the labia.

According to the inter-labial pad of the present invention, since it comprises a pressure following-up recoverable structure having predetermined compressibility and bulk recoverability responding to an inter-labial pressure caused to the inter-labial pad from the right and left sides of the labia in the state of wearing, it is properly compressed responding to pressurization caused to the inter-labial pad, and sufficiently recovers the bulk when the pressure caused to the inter-labial pad is released. Accordingly, no gap is formed between the labial inner wall and the inter-labial pad responding to the fluctuation of the pressure caused from the right-to-left directions, and can prevent the risk for the leakage of the menstrual blood and detachment of the inter-labial pad from labia.

For example, in the absorbent body constituted with fibers capable of absorbing a body fluid, the fibers can be oriented to a predetermined direction by a manufacturing method or a post treatment. In a case where the direction of the fibers is aligned with respect to the longitudinal direction of the inter-labial pad, when a pressure is applied from the labial inner wall in the right-to-left direction in the state of wearing to the inter-labial pad, the fibers tend to intrude easily between other fibers. As a result, the inter-fiber distance is shortened and the thickness of the absorbent body is reduced to lower the bulk recoverability. Particularly, in a state of absorbing menstrual blood, since the fibers tend to slip more easily to each other, the fibers are more liable to intrude between other fibers to further lower the bulk recoverability.

On the contrary, in the present invention, since the fiber orientation of at least a portion of the fibers constituting the inter-labial pad is aligned so as to be along the right-to-left direction which corresponds to the direction of fluctuation caused by the inter-labial pressure in the state of wearing, the inter-fiber distance is not shortened excessively due to the fiber rigidity responding to the fluctuation of the pressure caused from the right and left sides of the labial inner walls, between which the inter-labial pad is put and, even if it is shortened, since the recovering force due to the fiber rigidity exerts in a case where the inter-labial pressure is released, the thickness of the inter-labial pad tends to return easily to the original state. Accordingly, it can appropriately follow-up the fluctuation of the pressure in the right-to-left directions of the labial inner walls between which the pad is put, thereby capable of preventing the risk of leakage of the menstrual blood and detachment of the inter-labial pad from the labia.

In the present invention, "orienting so as to direct in the right-to-left direction" means orienting to a direction which is parallel with the ground surface in the state of wearing the inter-labial pad and is vertical to pudential slit. Further, for the orientation of the fibers constituting the inter-labial pad, either the orientation of at least a portion of fibers may be aligned in the right-to-left directions, for example, in a case of using an embossing to be described later, or the orientation of the entire fibers is aligned in the right-to-left direction.

The pressure following-up recoverable structure may be provided to the fiber aggregate constituting the inter-labial pad. Specifically, the pressure following-up recoverable structure may be provided to a surface side sheet, an absorbent body, a back face sheet having a fiber aggregate or other third member having a fiber aggregate alone or in a composite form thereof. The third member may be disposed on a surface of the surface side sheet, may be disposed between the surface side sheet and the absorbent body or between the absorbent body and the back face sheet in a case where it comprises a material having affinity with liquid, and it may be disposed either between the absorbent body and the back face sheet or may be disposed on the back face of the back face sheet in a case where it comprises a material not having affinity with liquid.

Cases where the inter-labial pressure to the inter-labial pad increases in the state of wearing include, for example, a case where a wearer takes an attitude of sitting on a chair. Further, cases where the inter-labial pressure to the inter-labial pad is released include, for example, a case where a wearer takes an attitude of standing up from the chair.

The compressibility means a property of decreasing the thickness of the inter-labial pad when the inter-labial pad is pressed at a predetermined pressure and for a predetermined time in the present specification. Further, the bulk recoverability means a property of increasing the thickness of the inter-labial pad when it is left with no pressure for a predetermined time after it has been pressed at a predetermined pressure and for a predetermined time.

The necessary constitution for the inter-labial pad is to have at least an absorbent body constituted with fibers capable of absorbing the menstrual blood, and it is not particularly limited. For example, it includes a constitution of consisting only of the absorbent body or a constitution of consisting of the absorbing covered with a liquid pervious sheet, a constitution of forming a laminate comprising a surface side sheet/an absorbent body/a back face sheet shaped into a loop and, a constitution of folding a laminate comprising a surface side sheet/an absorbent body/a back face sheet folded along a crease as will be described later.

(2) The inter-labial pad according to (1), wherein the absorbent body comprised absorbing fibers capable of absorbing the body fluid, and
the pressure following-up recoverable structure is formed by orienting at least a portion of the absorbing fibers constituting the absorbent body so as to direct in the right-to-left direction.

According to this embodiment, since the fibers (absorbing fibers) constituting the absorbent body capable of absorbing the body fluid are oriented to a predetermined direction by a manufacturing method or a post treatment thereof, this embodiment is particularly suitable to the present invention. As a method of orienting the absorbing fibers constituting the absorbent body in the direction of the thickness of the laminate, fiber orientation may be applied during sheeting of the absorbent body, or a post treatment such as enforcing the fiber orientation after the sheeting may be applied.

(3) The inter-labial pad according to (1) or (2), wherein the inter-labial pad comprises a laminate having a surface side sheet in contact with the labia in the state of wearing, a back face sheet disposed so as to stack over the surface side sheet and not in contact with the labia, and the absorbent body disposed between the surface side sheet and the back face sheet, in which
the inter-labial pad is of a substantially longitudinal shape having a longitudinal direction and a lateral direction, and is folded such that a pair of portions of the back face sheet are opposed to each other along a longitudinal crease of the laminate in wearing, and
at least a portion of the inter-labial pad put between the labia has the pressure following-up recoverable structure.

According to this embodiment, occurrence of the gap can be prevented easily by merely folding in two and, further, the gap can be prevented more easily by applying the pressure following-up recoverable structure. The gap can be prevented easily as described above by merely folding because the absorbent body extending from the crease as an axis to both the right-to-left directions is disposed corresponding to the labial inner wall extending from the vestibular floor as an axis to both the right-to-left direction so that the inter-labial pad can easily follow up the change of behavior of the labia. For example, in a case where the labia opens such that the right and left labial inner walls recede with the vestibular floor as an axis, also the right and left parts of the absorbent body can open following up the same with the crease as the axis. Then, in the present invention, since the pressure following-up recoverable structure is also applied in addition to the constitution described above, risk of the body flood leakage or detachment of the inter-labial pad from the labia can be prevented more reliably.

(4) The inter-labial pad according to (3), wherein the pressure following-up recoverable structure is disposed symmetrically with the crease of the laminate as an axis of symmetry.

According to this embodiment, the inter-labial pad compresses and the bulk recover uniformly to both right and left side of the labial inner walls without slanting either side. Therefore, the occurrence of a gap between only one side of the labial inner wall and the inter-labial pad can be prevented.

(5) The inter-labial pad according to (3) or (4), wherein the pressure following-up recoverable structure is formed by orientating the absorbing fibers constituting the absorbent body in the direction of the thickness of the laminate.

According to this embodiment, by orienting the fibers constituting the absorbent body in the direction of the thickness of the laminate, the direction of fibers constituting the absorbent body can be aligned to be along the right-to-left direction in which the inter-labial pressure is caused in the inter-labial pad in the state of wearing when it is folded in two. Accordingly, the inter-labial pad can properly follow-up the fluctuation of the inter-labial pressure and it is possible to prevent the risk of leakage of the menstrual blood and detachment of the inter-labial pad from the labia. Further, as a method of orienting the fibers constituting the absorbent body to the direction of the thickness of the laminate, for example, a treatment of enforcing the fiber orientation may be applied during sheeting of the absorbent body, or a post treatment of enforcing the fiber orientation may be applied after sheeting.

(6) The inter-labial pad according to (5), wherein the absorbing fibers are oriented by applying concave/convex fabrication to the absorbent body.

According to the embodiment, since the fibers can be compulsorily aligned to a predetermined direction by the concave/convex pattern, the absorbing fibers constituting the absorbent body can be oriented in the direction of the thickness of the absorbent body in the same manner as in (5) described above.

(7) The inter-labial pad according to any one of (1) to (6), wherein the absorbing fibers constituting the absorbent body are crimped fibers.

According to this embodiment, since the crimped fibers tend to cause partial fiber orientation and are excellent in the recoverability in a case where they are compressed so as to shrink, the bulk recoverability is enhanced and, accordingly, it is suitably usable particularly to the present invention.

(8) The inter-labial pad according to any one of (1) to (7), wherein at least a portion of the absorbing fibers constituting the absorbent body is synthetic fibers.

According to this embodiment, since the synthetic fibers are poor in the water absorbability, the fiber rigidity can be retained easily also in a case of absorbing the menstrual blood in a state of wearing the inter-labial pad. Accordingly, the compressibility and the bulk recoverability can be maintained during wearing.

(9) The inter-labial pad according to any one of (1) to (8) wherein an elastic sheet is disposed to a portion of the inter-labial pad to be put between the labia.

According to this embodiment, since the elastic sheet having a high bulk recoverability is provided, even when the inter-labial pressure fluctuates excessively, for example, by playing sports, a gap is less caused between the inter-labial inner wall and the inter-labial pad.

(10) The inter-labial pad according to any one of (1) to (9), wherein the predetermined compressibility and the bulk recoverability are formed such that they are higher in the forward portion of the inter-labial pad situating at the front of a wearer compared with those in the backward portion of the inter-labial pad situated at the back of the wearer in the state of wearing the inter-labial pad.

According to the embodiment, the compressibility and the bulk recoverability are made higher in the forward portion of the inter-labial pad situated at the front of the wearer compared with those of the backward portion situated at the back of the wearer. In this regard, since the forward portion of the labia minus pudendi is thicker and longer than the backward portion thereof with respect to the shape, the inter-labia pressure is higher and the fluctuation of the inter-labia pressure is larger in the forward portion. Accordingly, the following-up property of the inter-labia pad to the fluctuation of the inter-labial pressure can be improved further by controlling the compressibility and the bulk recoverability higher in the forward portion than in the backward portion of the inter-labial pad.

(11) The inter-labial pad according to (10), wherein the inter-labial pad is applied with slitting from the forward portion to the backward portion.

According to this embodiment, the higher inter-labia pressure in the forward portion and the lower inter-labial pressure in the backward portion can be separated by applying slitting to the inter-labial pad. This can prevent a high inter-labial pressure from being exerted particularly on the backward portion of the inter-labial pad.

(12) The inter-labial pad according to any one of (1) to (11), wherein the predetermined compressibility and bulk recoverability are the compressibility and the bulk recoverability in a moistened state of absorbing the body fluid.

Generally, the compressibility and the bulk recoverability of fibers are remarkably lowered in the absorbent body, particularly, in a moistened state. However, according to this embodiment, since preferred compressibility and bulk recoverability are provided in the moistened state of absorbing the body fluid, this can effectively prevent the risk of the leakage of the menstrual blood, etc. and the detachment of the inter-labial fluid from the labia.

(13) The inter-labial pad according to any one of (1) to (12), wherein the predetermined compressibility and bulk recoverability of the inter-labial pad after it has absorbed an artificial body fluid about seven time as much as the mass of the absorbent body provide (a) a compression ratio in which the thickness of the inter-labial pad after it has been pressed at a pressure of 50 g/cm$^2$ for 3 min is 30% or more relative to the thickness of the inter-labial pad before it absorbs the artificial body fluid, and (b) a bulk recovery ratio in which the thickness of the inter-labial pad after it has been pressed at the pressure of 50 g/cm$^2$ for 3 min, and, further, left under no pressure for 2 min is 60% or more relative to the thickness of the inter-labial pad before it absorbs of the artificial body fluid.

According to this embodiment, since the compression ratio in the state of absorbing the artificial body fluid by the method described above is 30% or more, even in a state where the inter-labial pressure is exerted on the inter-labial pad, the pad can easily deform under compression confirming the change of the shape of the labia and the inter-labial pad can follow-up the change. Further, since the bulk recovery ratio in the state of absorbing the artificial body fluid is 60% or more, even in a state where the inter-labial pressure lowers, the inter-labial pad follows-up the labial inner wall under bulk recovery.

The thickness of the inter-labial pad in the present invention is a thickness assuming the state of wearing the inter-labial pad and, in the state of use where the laminate is folded in two, it means the total thickness in the folded state.

(14) The inter-labial pad according to (13), wherein the compression ratio is 30% or more and 80% or less, and the bulk recovery ratio is 60% or more and 150% or less.

According to this embodiment, since the compression ratio in the state of absorbing the artificial body fluid by the method described above is 80% or less, it is possible to prevent discharge of the body fluid once absorbed under excess compression. Further, since the bulk recovery ratio is 150% or less, it is possible to prevent excess urging of the labial inner wall. Particularly, in a case where the bulk recovery ratio is within a range from 100 to 150%, this means the volume increases to more than the volume before absorption of the artificial body fluid and, since this can reduce the volume upon insertion of the inter-labial pad, a wearer can easily insert the inter-labial pad in a narrow gap between labia and can easily attach the pad to a position reliably.

(15) The inter-labial pad according to any one of (1) to (12), wherein the thickness of the inter-labial pad before it absorbs the artificial body fluid is from 3 mm to 10 mm, and the thickness of the inter-labial pad after it has been pressed at a pressure of 50 g/cm² for 3 min and further left under pressure for 2 min in a state where the inter-labial pad absorbs the artificial body fluid about seven times as much as the mass of the absorbent body.

According to this embodiment, since the thickness of the inter-labial pad after releasing the pressurization in a state of absorbing the artificial body fluid is 3.8 mm or more, even in a state where the inter-labial pressure lowers, the pad can follow-up without causing a gap between the labial inner wall and the inter-labial pad. Further, since this is 15 mm or less, it can prevent excess urging on the labial inner wall.

This invention can provide an inter-labial pad capable of flexibly following-up the pressure fluctuation in a case where an inter-labial pressure in the right-to-left direction of a wearer exerts on the inter-labial pad, for example, as in the attitude where a wearer is sitting on a chair, standing up from the chair or during vigorous movement and can provide an inter-labial pad of less leaking the menstrual blood from the inter-labial pad and less detaching the inter-labial pad from the labia.

"DESCRIPTION OF THE SYMBOLS"

Figure 1:
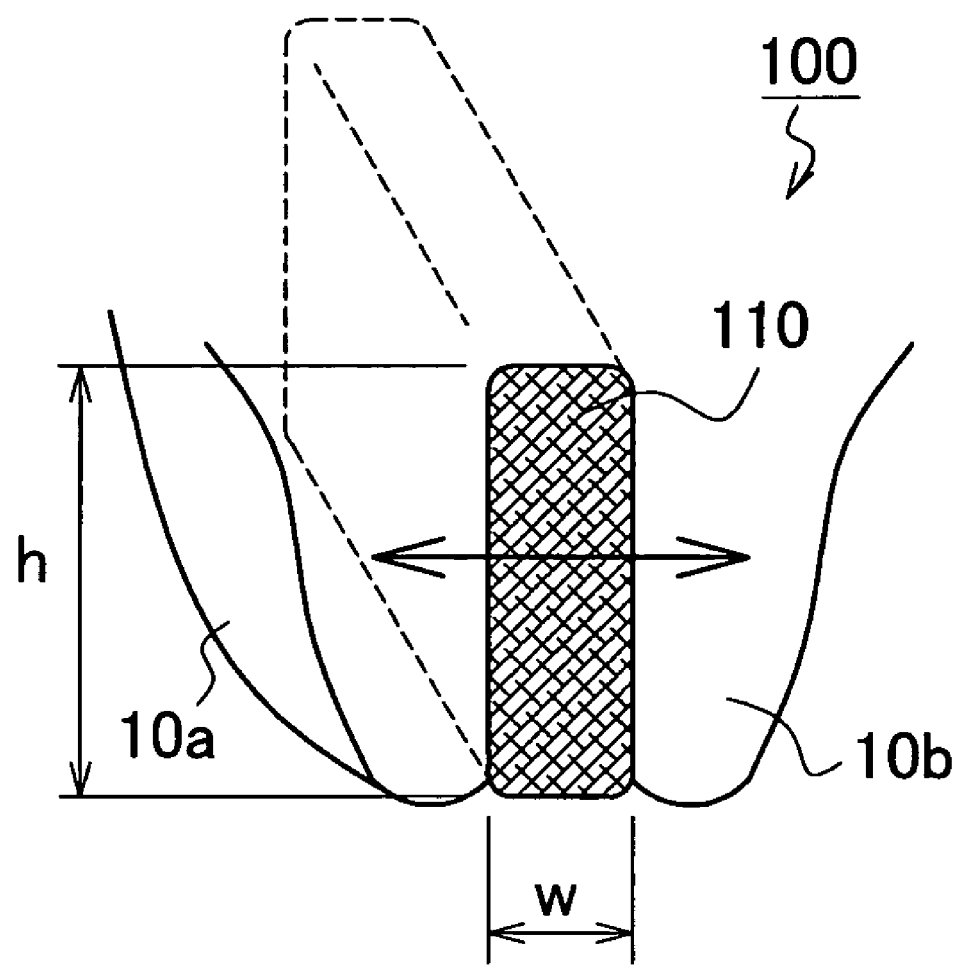
FIG. 1 is a perspective view showing the state of wearing an inter-labial pad according to a first embodiment of the invention.

| | |
|---|---|
| 10, 10a, 10b | inter-labia |
| 100, 300, 400, 500, 600 | inter-labial pad |
| 110, 310, 410, 510, 610 | absorbent body |
| 311, 411, 511 | crease |
| 415 | convex portion |
| 416 | concave portion |
| 512 | embossing |
| 620 | surface side sheet |
| 630 | back face sheet |
| 650 | elastic sheet |
| 660a, 660b, 660c | slit |

DESCRIPTION OF THE PREFERRED EMBODIMENTS

Preferred embodiments of the present invention is to be described with reference to the drawings. In the subsequent descriptions for the embodiments, identical constituent factors carry identical reference numerals for which descriptions will be omitted or simplified.

First Embodiment

<State of Using Inter-Labial Pad>

FIG. 1 shows a state of using an inter-labial pad 100 according to a first embodiment of the present invention. As shown in FIG. 1, the inter-labial pad 100 has a substantially rectangular shape as a whole and is attached to labia so as to be put between wearer's labia 10a and 10b. The inter-labial pad 100 comprises a substantially rectangular absorbent body 110.

The absorbent body 110 is constituted with fibers capable of absorbing menstrual blood and the direction of the fibers are aligned, in a state of wearing, along the direction 10a to 10b in which the inter-labial pressure is caused, that is, in the direction of an arrow in FIG. 1.

<Manufacturing Method of Absorbent Body>

Figure 2:
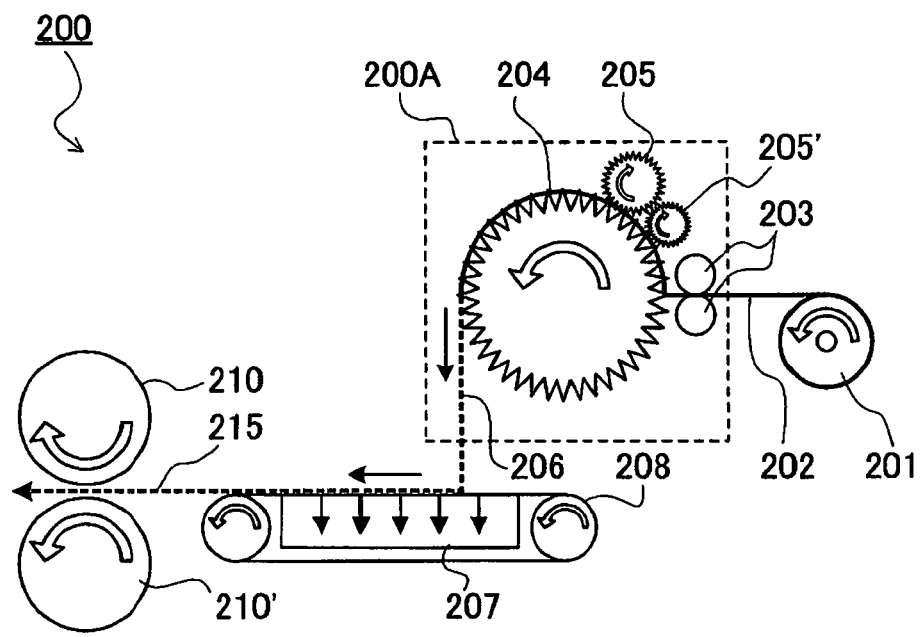
FIG. 2 is a schematics view of an apparatus for fiber opening and laminating fibers for manufacturing an inter-labial pad according to the first embodiment of the invention.
Figure 3:
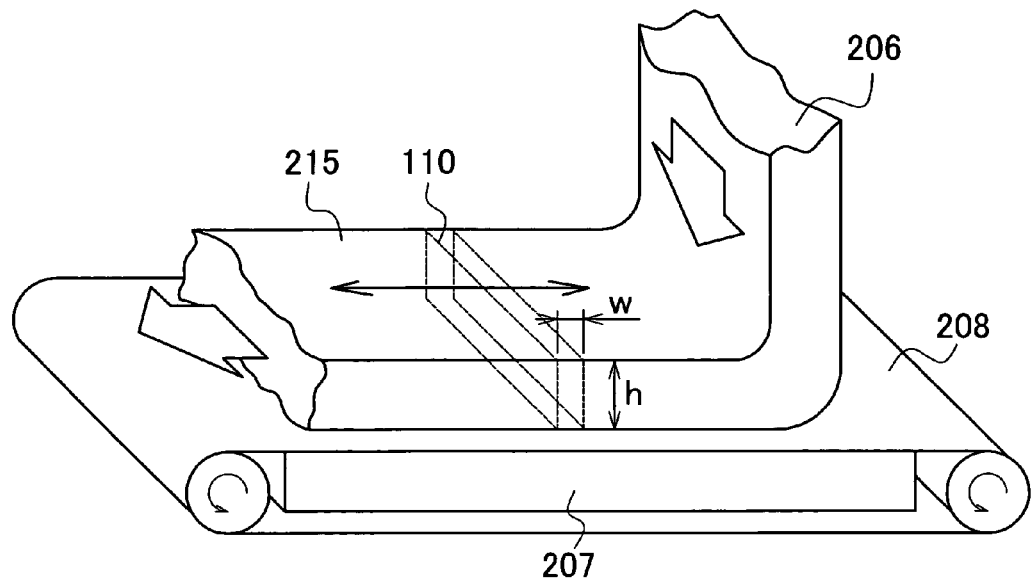
FIG. 3 is an enlarge perspective view showing an example for a portion of a lamination device in FIG. 2.

FIG. 2 and FIG. 3 are views showing an example for a method of manufacturing the absorbent body 110 in which FIG. 2 is a schematic view of an apparatus for fiber opening and laminating fibers and FIG. 3 is an enlarged perspective view for a portion of the laminating device shown in FIG. 2. As shown in FIG. 2, the apparatus 200 mainly comprises a fiber opening device 200A for opening fibers, and a conveyor belt 208 for conveying opened fibers at a predetermined speed and sheeting them. At first, the fiber aggregate before fiber opening is taken up as a take-up roll 201. Then, a fiber aggregate sheet 202 is delivered therefrom and conveyed by a pair of rolls 203 to the fiber opening device 200A.

The fiber opening device 200A has a garnet type fiber opening roll 204 in which corrugating blades are arranged in plurality and the fiber aggregate sheet 202 is passed over the fiber opening roll 204 to be opened. In this case, for enhancing the fiber opening performance, it is more preferred that a plurality of rolls 205, 205' in which tips of corrugating blades arranged in plurality and adjacent with each other are disposed alternately in a zigzag manner are combined such that they rotate in the direction opposite to the rotational direction of the fiber opening roll 204 for passing the fiber aggregate. The method for fiber opening the fiber aggregate is not particularly restricted but selected, for example, from a garnet type and a hammer mill type. It is preferred to conduct fiber opening by the garnet type in which the corrugating blades less fracturing the fibers are arranged in plurality. Further, for enhancing the fiber opening performance more, a plurality of rolls may be combined such that they rotate in the directions opposite to each other. Further, they may be disposed in a zigzag manner such that the tips of corrugating blades arranged in plurality and adjacent with each other are arranged alternately.

A fiber aggregate 206 fibers of which have thus opened is drawn under suction from a suction device 207 disposed to the inner surface of a mesh-shaped conveyor belt 208 and laminated as the fiber aggregate 206 on the conveyor belt 208. Then, a collection speed is given to the opened fiber aggregate 206 by suction soon after the fibers have left from the corrugating blades of the fiber opening roll 204.

In a case where the conveying speed of the conveyor belt 208 is relatively higher than the collection speed of the fiber aggregate 206, fibers are oriented in the MD direction which is the direction of the arrow in FIG. 2 to form an oriented fiber aggregate 215 and, finally, passed through the rolls 210, 210' to form a sheet. The MD direction is an advancing direction of the conveyor belt 208, that is, the advancing direction of the fiber aggregate 206. As described above, the fiber orientation of the fiber aggregate collected by the conveyor belt 208 can be mainly controlled by the relative difference between the collection speed and the conveying speed.

As shown in FIG. 3, fibers are oriented in the MD direction and an absorbent body 110 is cut into a rectangular shape as shown by dotted lines in FIG. 3, that is, so as to have a width w and a height h in the state of wearing the inter-labial pad 100 in FIG. 1. Then, when it is inserted as in the illustrated state between the labia as shown in FIG. 1, the fiber directions can be aligned in the direction of 10a to 10b in which the inter-labial pressure is caused, that is, in the direction of the arrow shown in FIG. 1, in the state of wearing.

<Fiber Constitution>

Fibers constituting the absorbent body 110 preferably have a fiber rigidity for obtaining appropriate compressibility and bulk recoverability. The fiber rigidity is generally expressed by Young's modulus (=load/strained amount). In this invention, it is preferred to use fibers having Young's modulus in a range from 100 to 1500 kg/mm$^2$ and, more preferably, in a range from 300 to 1000 kg/mm$^2$. Further, the fiber rigidity can also be controlled by changing the fiber denier and, specifically, it is preferably selected in a range from 1.1 to 8.8 dtex.

For the materials of the fibers, natural pulp, chemical pulp, rayon, acetate, natural cotton, super absorbent polymer, super absorbent polymer fiber, synthetic fiber, etc. are used. They may be used alone or a plurality of them may be mixed. Further, it is preferred that they are bulky, less deforming and giving less chemical stimulations.

Among those described above, it is preferred that at least a portion of the fibers constituting the absorbent body is synthetic fibers. Since the synthetic fibers are poor in the water absorbability, they tend to easily maintain fiber rigidity even when they absorb menstrual blood in a state of wearing the inter-labial pad. Accordingly, compressibility and bulk recoverability can be maintained during wearing. The synthetic fibers include, for example, polyethylene (PE) fibers, polypropylene (PP) fibers, polyethylene terephthalate (PET) fibers, polyamide (PA) fibers, acrylic fibers, etc. with no particular restriction to them.

In order to provide compressibility without giving a foreign-body sensations to a wearer, "bulky" materials are preferred. For example, it is preferred to use physically embossed rayon or acetate.

As the "bulky" materials, crimped fibers having crimped structure are also preferred. The crimped fibers include chemical pulp crimped by cross linking using a cross linker, composite fibers such as of PE, PP, PET, etc. described above, which are composite fibers of a core-sheath type, core-sheath eccentric type or side-by-side type by utilizing the difference of the heat shrinkage of respective resins, and those physically crimped spun fibers by engagement, embossing, etc. Further, those enhanced for the molecular orientation by stretching in a state of spinning, or fibers having a profiled cross section such as Y- or C-type cross sectional shape may also be mixed.

Furthermore, fibers having the Young's modulus within the range described above and in the form of crimped fibers are more preferred since the fiber orientation partially tends to be directed rightward and leftward, which is substantially the direction of the arrow in FIG. 1, they tend to be compressed easily so as to be crimped and tend to recover the original shape. Further, for improving the slipping property between the fibers, an oil agent may be coated on or contained in the fibers.

For the fiber length, longer fibers are more likely to be entangled for sheeting the collected fiber aggregate, that is, for entangling fibers to each other with the fiber orientation being aligned. Specifically, it is preferred that the fiber length is within a range from 10 to 51 mm and it is more preferred to use mainly those fibers with the average fiber length of from 25 to 50 mm.

Specific examples of the fibers described above include mixed fibers comprising (a) from 5 to 100% of synthetic fibers which are of a core-sheath eccentric type of PE and PP, having a fiber denier of 4.4 dtex, a fiber length of 51 mm, and a fiber crimping ratio of 60%, with 0.2% of a hydrophilic oil agent being deposited and (b) from 95 to 0% of rayon having a fiber denier of 3.3 dtex, a fiber length of 51 mm, and a fiber crimping ratio of 50%, with 0.2% of a hydrophilic oil agent being deposited.

They are formed into an oriented fiber aggregate 215 in FIG. 2 by relatively increasing the conveying speed to be more than the collection speed. Then, they may be embossed by a dot-shaped emboss pattern, for example, by constituting the rolls 210, 210' as dot-shaped emboss rolls. In addition to the synthetic fibers and rayon, it is also preferred to incorporate super absorbent polymer or highly compressed fiber lumps. Since this expands the volume after absorbing a body fluid, etc. the volume can be increased relative to the volume before absorbing the body fluid to obtain a further high bulk recoverability.

Further, as other highly bulky and less deforming oriented fiber aggregate 215 than described above, non-woven fabric sheeted by a through air method using a plurality kinds of synthetic fibers may also be used alone or being stacked by plural sheets.

<Other Example for the Manufacturing Method of Absorbent Body>

Figure 4:
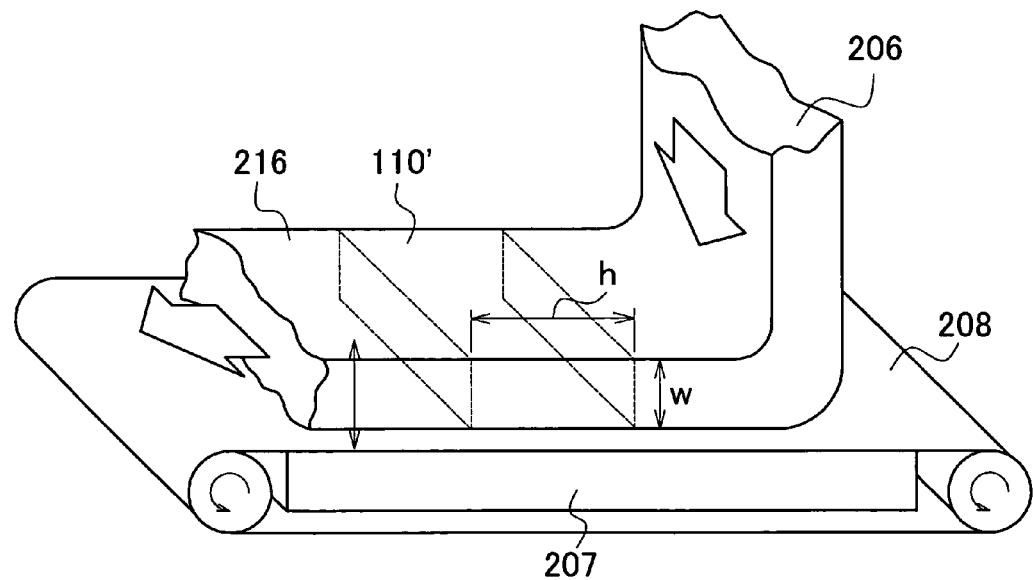
FIG. 4 is an enlarge perspective view showing another example for a portion of a lamination device in FIG. 2.

FIG. 4 shows another manufacturing method for aligning the direction of fibers constituting an absorbent body 110 as shown in FIG. 1. In this method, contrary to FIG. 3, the conveying speed of the conveyor belt 208 is relatively lower than the collection speed of the fiber aggregate 206. In this case, the fiber orientation of the oriented fiber aggregate 216 is in the direction of the thickness of the oriented fiber aggregate 216 which is the direction of the arrow in FIG. 4.

In this case, as shown by dotted lines in FIG. 4, an absorbent body 111 is cut in a rectangular shape such that the width w corresponds to the direction of the thickness for the oriented fiber aggregate 216 and the height h corresponds to the MD direction of the oriented fiber aggregate 216 in FIG. 1. Then, when this is put between labia in a state being inverted from the state shown in FIG. 4 by 90°, the direction of the fibers can be aligned in the direction of 10a to 10b in which the inter-labial pressure is caused, that is, in the direction of the arrow shown in FIG. 1 in a state of wearing.

Fibers of oriented fiber aggregate 216 can be directed to the direction of the thickness by selecting the suction pressure caused to the collected fibers aggregate by way of the mesh-like conveyor belt 208 within a range from 1500 to 15000 Pa, for example, in a case where the conveying speed is within a range from 20 to 200 m/min. When the suction pressure is lower than 1500 Pa, the fibers tend to be directed in the MD direction by the conveying speed. On the other hand, when it is higher than 15000 Pa, the fibers are excessively entangled to the mesh of the conveyor belt, making it difficult to hand the fiber aggregate to the succeeding step. In a case where the suction pressure is selected within a range from 1500 to 15000 Pa, since a collection speed of 4 to 20 m/sec (240 to 1200 m/min) is given to the fibers, and the conveyor belt is conveyed in a range of a speed from 20 to 200 m/min, so that the collection speed given to the fibers becomes relatively higher and the fiber orientation is less directed to MD.

Further, after collection, it is necessary that the fiber aggregate is not stretched but conveyed in a state where the fiber orientation in a collected state is substantially maintained as it is. It is preferred not to stretch the fiber aggregate, 216 particularly before embossing step (by rolls 210, 210') provided for controlling the degree of freedom for the collected oriented fiber aggregate 216. This is because the fiber orientation of the fiber aggregate is easily directed to the MD direction when the fiber aggregate has been stretched in any steps before embossing, since the degree of freedom of the fiber aggregate is excessively high. Accordingly, it is necessary not to excessively increase the surface speed of the emboss rolls (210, 210') for conducting embossing relative to the surface speed of the conveyor belt 208 on which the fiber aggregate is collected and, specifically, it is preferred that the ratio between the surface speed of the emboss roll and the surface speed of the conveyor belt (surface speed of emboss roll/surface speed of conveyor belt) is preferably within a range from 0.9 to 1.2 and, more preferably, within a range from 1.0 to 1.1. On the other hand, as shown in FIG. 3, for directing the fiber orientation of the fiber aggregate mainly to the MD direction, the condition may be set in the manner opposite that described above.

Second Embodiment

<State of Using Inter-Labial Pad>

Figure 5:
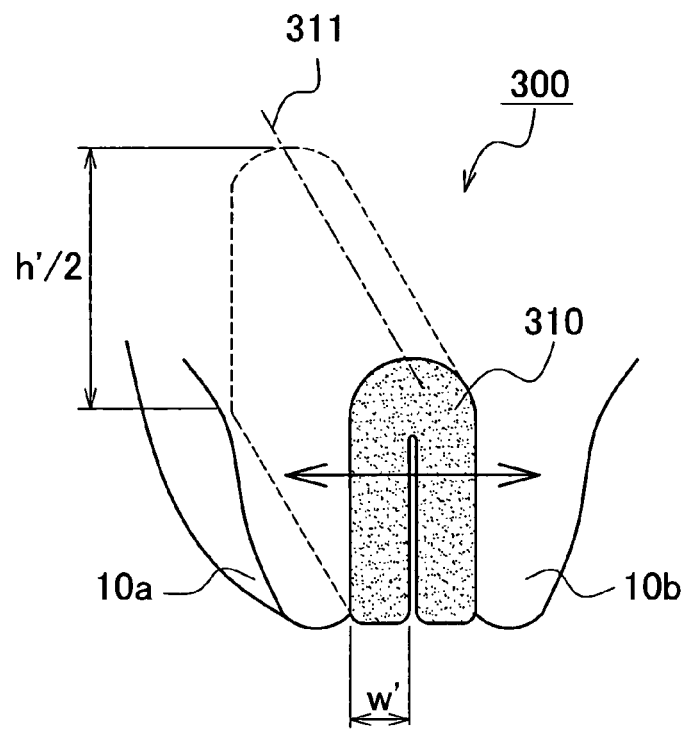
FIG. 5 is a perspective view showing the state of wearing an inter-labial pad according to a second embodiment of the invention.

FIG. 5 shows the state of using an inter-labial pad 300 according to a second embodiment of the present invention. As shown in FIG. 5, the inter-labial pad 300 is constituted such that an absorbent body 310 is folded in two along a crease 311 and a portion along the crease 311 being put between the labia 10a and 10b.

<Manufacturing Method of Absorbent Body>

Figure 6:
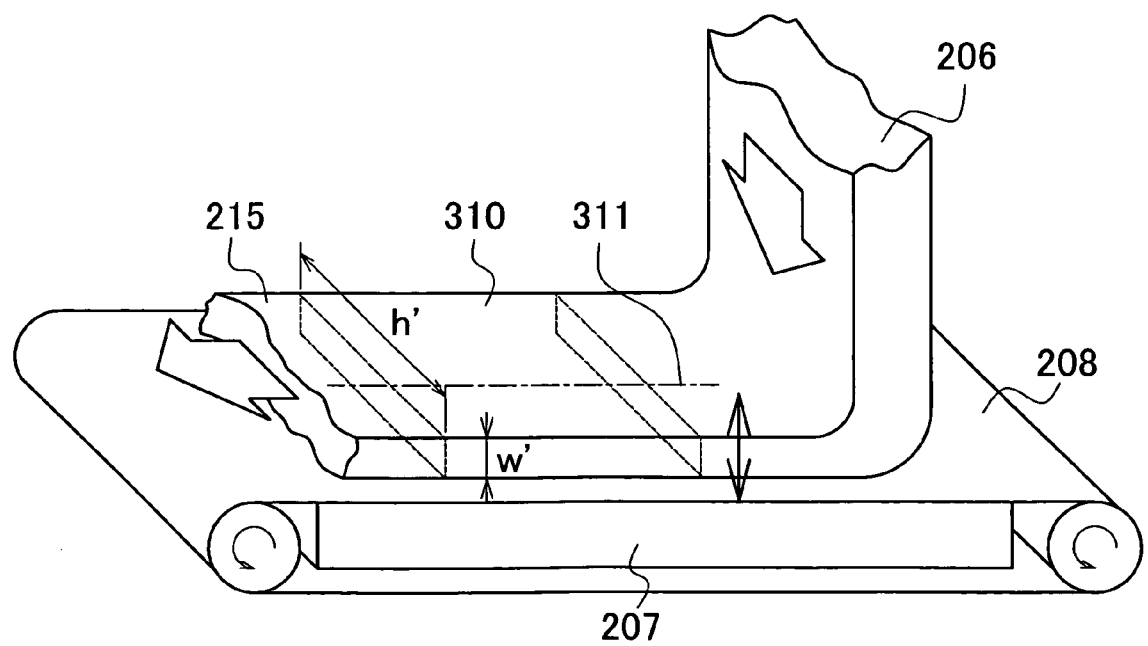
FIG. 6 is a perspective view of a laminating device for manufacturing an inter-labial pad according to the second embodiment of the invention.

FIG. 6 shows an example for the method of manufacturing an absorbent body 310. In the same manner as shown in FIG. 4, the conveying speed of a conveyor belt 208 is relatively lower to the collection speed of fibers 206. Accordingly, the fiber orientation of an oriented fiber aggregate 216 is in the direction for the thickness of the oriented fiber aggregate, which is the direction of an arrow shown in FIG. 6.

In this case, the absorbent body 310 is cut into a rectangular shape by the dotted lines as shown in FIG. 6 such that the width w' in FIG. 5 corresponds to the direction of thickness for the oriented fiber aggregate 216 in FIG. 6, doubled height for h'/2 in FIG. 5 corresponds to the lateral direction h' of the oriented fiber aggregate 216. Then, when it is folded along the crease 311 and put between the labia, the fiber direction can be aligned along the direction of 10a to 10b in which the inter-labial force is caused in a state of wearing. That is, fibers may be aligned in the direction of the arrow in FIG. 1.

Third Embodiment

<State of Using the Inter-Labial Pad>

Figure 7:
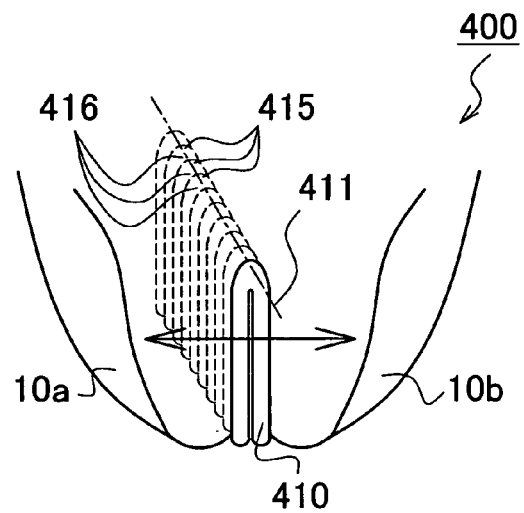
FIG. 7 is a perspective view showing the state of wearing an inter-labial pad according to a third embodiment of the invention.

FIG. 7 shows a state of using an inter-labial pad 400 according to a third embodiment of the present invention. As shown in FIG. 7, the inter-labial pad 400 is different from that shown in FIG. 5 in that a convex portions 415 and a concave portion 416 are formed alternately along the direction vertical to a crease 411 on the surface of an absorbent body 410.

<Manufacturing Method of Absorbent Body>

Figure 8:
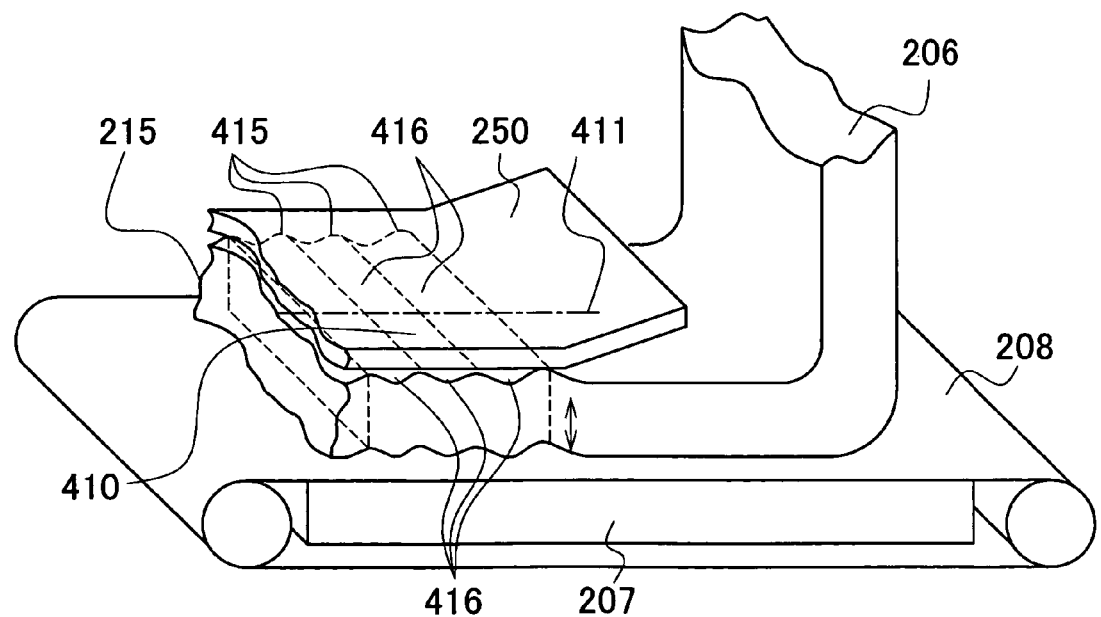
FIG. 8 is a perspective view of a laminating device for manufacturing an inter-labial pad according to the third embodiment of the invention.

The absorbent body 410 can be obtained by the manufacturing method as shown in FIG. 8. That is, as shown in FIG. 8, a plate 250 that gradually restricts the thickness of the fiber aggregate 206 is located above a conveyor belt 208. Since the plate 250 constitutes resistance to the fiber aggregate 206 being conveyed and the fiber aggregate 206 is conveyed being deformed in a corrugated shape, the fiber orientation of the fiber aggregate is directed to the direction of the thickness as a whole. In the succeeding step, the absorbent body 410 is cut into a substantially rectangular shape having a corrugated surface by the dotted lines as shown in FIG. 8. Then, when it is folded along a crease 311, and put between the labia, the fiber direction can be aligned along the direction of 10a to 10b in which the inter-labial pressure is caused, that is, in the direction of the arrow in FIG. 7.

In addition to the method described above, the conveyor belt 208 may be previously formed into a corrugated shape upon collecting the fiber aggregate 206. Also in this constitution, the fiber aggregate 206 is collected profiling the shape of the conveyor belt 208.

Fourth Embodiment

<State of Using Inter-Labial Pad>

Figure 9:
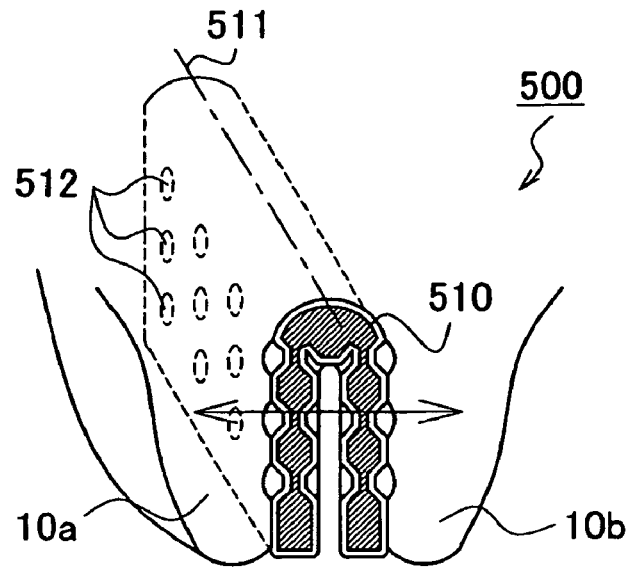
FIG. 9 is a perspective view showing the state of wearing an inter-labial pad according to a fourth embodiment of the invention.

FIG. 9 shows a fourth embodiment of an inter-labial pad according to the present invention. An inter-labial pad 500 is different from the embodiment shown in FIG. 5 in that embossing 512 is applied to the surface of an absorbent body 510. Reference numeral 511 denotes a crease.

<Manufacturing Method of Absorbent Body>

Such embossing can be conducted, for example, by constituting rolls 210, 210' in FIG. 2 as emboss rolls. That is, by embossing, since the fiber orientation at the portion is partially aligned in the direction of the thickness of the fiber aggregate, the same effect as that of the embodiment described above can be obtained. An emboss pattern is not particularly limited so long as the fiber orientation is directed to the direction of the thickness of the fiber aggregate and it may be a dot-shape or lattice-shape, as well as a corrugated shape causing deformation as shown in FIG. 8. Among them, a dot-shape emboss pattern is preferred considering a flexibility giving less foreign-body sensation to a wearer.

Specifically, embossing can be applied, for example, by a dot-shape emboss pattern arranged in a zigzag manner with an embossing area ratio of 0.5%, a pin diameter of 1.0 mm and a pitch of 12.5 mm. With this constitution, since the fiber orientation is partially directed to the direction of the thickness at the instance the fibers are collected and, in addition, fibers at the periphery of the dot-like embossing are enforced by the pins in the direction of the thickness and joined by hot melting, the fiber orientation at the periphery of the dot-shape embossing is further directed to the direction of the thickness and becomes more firm. The dot-shape embossing area ratio is, preferably, within a range from 0.3 to 60%.

As other examples than the embossing as described above of controlling the fiber orientation upon sheeting the collected fiber aggregate, a needle punching manufacturing method of directing the fiber orientation at the needled portion to the direction of the thickness by applying needling in the direction of the thickness thereby entangling the fibers to each other, and a spun lace manufacturing method of hitting a water jet in the direction of the thickness thereby directing the fiber orientation at the portion undergoing a water pressure to the direction of the thickness and entangling the fibers to each other by the water jet, etc. may also be used.

Fifth Embodiment

<State of Using Inter-Labial Pad>

Figure 10:
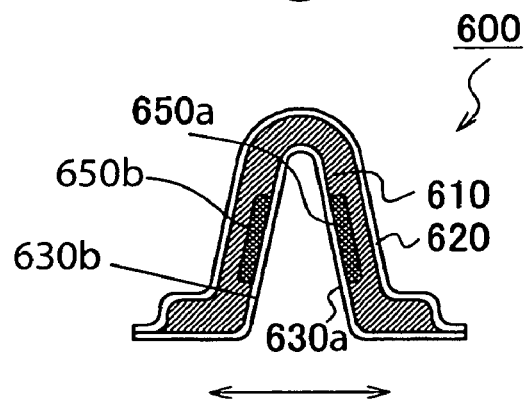
FIG. 10 is a cross sectional view of an inter-labial pad according to a fifth embodiment of the invention.
Figure 11:
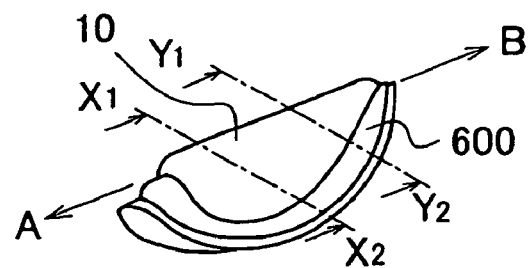
FIG. 11 is a perspective view showing the state of wearing the inter-labial pad according to the fifth embodiment of the invention.
Figure 12:
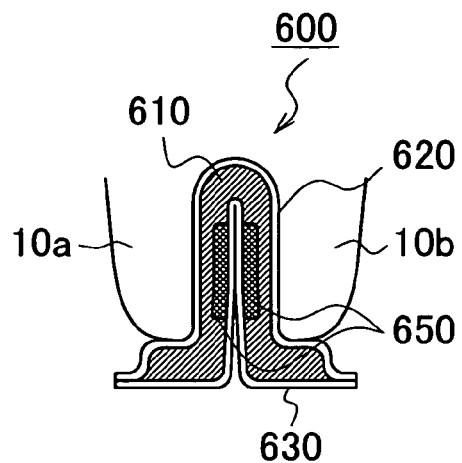
FIG. 12 is a cross sectional view taken along line $X_1$-$X_2$ in FIG. 11.
Figure 13:
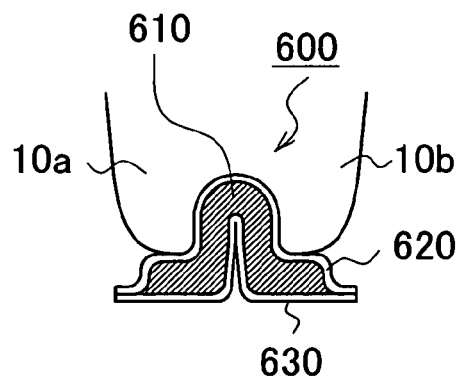
FIG. 13 is a cross sectional view taken along line $Y_1$-$Y_2$ in FIG. 11.

FIG. 10 shows a fifth embodiment of an inter-labial pad according to the present invention. Further, FIG. 11 shows a perspective view showing a state of attaching the inter-labial pad according to the fifth embodiment, FIG. 12 is a cross sectional view taken along line $X_1$-$X_2$ in FIG. 11 and FIG. 13 is a cross sectional view taken along line $Y_1$-$Y_2$ in FIG. 11.

An inter-labial pad 600 comprises, as shown in FIG. 10, a surface side sheet 620 in contact with labia 10 in the state of wearing, a back face sheet 630 disposed so as to stack over the surface side sheet 620 and not in contact with the labia 10, an absorbent body 610 interposed between the surface side sheet 620 and the back face sheet 630, and a pair of portions 650a, 650b of at least one elastic sheet member 650 is disposed vertically centered between the longitudinal crease and bottom fold of the interlabial pad, each portion of the pair of portions 650a, 650b being interposed between the absorbent body 610 and the back face sheet 630 in symmetry with respect to the longitudinal center axis of the inter-labial pad 600. The absorbent body 610 prevents each portion 650a, 650b of the at least one elastic sheet member 650 from contacting the surface side sheet 620.

The inter-labial pad 600 is in substantially a longitudinal shape having a longitudinal direction and a shorter direction as a whole and folded along the longitudinal crease such that a pair of portions 630a, 630b of the back face sheet 630 are opposed to each other, and put with a portion along the crease being put between the labia. The fiber direction of the absorbent body 610 is aligned along the direction of the arrow in FIG. 10 like that in FIG. 5. Each portion of the pair of portions 650a, 650b is opposed to the other portion and each portion of the pair of portions 650a, 650b is in contact with a respective one of the pair of portions 630a, 630b of the back face sheet.

<Example of Elastic Sheet>

The location where the elastic sheet 650 is disposed is not particularly limited and it may be disposed between the surface side sheet 620 and the absorbent body 610, may be disposed in the absorbent body 610 or at the back of the back face sheet 630. The back face sheet 630 per se may be the elastic sheet 650. In view of the liquid absorbability and flexibility, the elastic sheet 650 is preferably disposed on the side of the absorbent body 610 at the back face sheet 630. Further, the elastic sheet 650 is preferably disposed in symmetrical with the crease as an axis of symmetry. Furthermore, it may be disposed so as to override the crease. The size of the elastic sheet 650 is not particularly limited and it is preferably equal with or less than the size of the absorbent body 610 in view of the flexibility. Further, for the thickness, it is preferably within a range from 0.5 to 5 mm in view of the flexibility.

As specific examples of the elastic sheet 650, laminates of elastic fibers, films, foamed materials having air cells, etc. can be mentioned.

The elastic fibers include thermoplastic materials such as PE, PP, PET, etc., and each of the resins is preferably used alone or as composite fibers of core-sheath type, core-sheath eccentric type, side-by-side type. Further, fibers applied with secondary crimping, for example, by mechanical crimping or heat are preferred because of more elasticity. In view of the feeling of wear with respect to elasticity and rigidity, those fibers controlled to a fiber denier of 0.5 to 88 dtex and a fiber length of 3 to 64 mm are used preferably.

A laminate of elastic fibers include non-woven fabrics. In this case, non-woven fabrics obtained by laminating fibers by carding, and being formed by a through air manufacturing method of bonding by hot melting of thermoplastic fibers can provide repulsive elasticity and can be used preferably. Generally utilized point bonding, spun bonding or spun lace method can also be utilized. Spun bonded non-woven fabrics of spinning continuous filaments and bonding them by heat embossing can also be utilized. Further, SMS (spun bonded layer/melt blown layer/spun bonded layer) non-woven fabrics bonded by blowing melt-blown fibers to spun bonds can also be utilized, and chemical bonding or an air laid method by coating a binder to the surface after the fiber lamination can also be utilized. The materials described above may be used in a single layer or may be multi-layered and fixed by an adhesive material or embossing. Further, those materials controlled for the compressibility or bulk recoverability to a predetermined direction by an embossing pattern can also be utilized preferably.

As the film, those materials obtained by extruding resins such as elastic PE, PP, PET or further higher elastic urethane or rubber by T-die or inflation method can be utilized. In the extrusion, a single material may be used, plural materials may be extruded as a multi-layered form, or plural layers may be laminated into a composite form.

As the foamed materials having air cells, those materials obtained by foaming resins such as elastic PE, PP or higher elastic urethane or rubber and, further, cellulose sponge having absorbability can be utilized. The foamed materials may be of open cell or closed cell type.

The elastic sheet 650 and the absorbent body 650 described above are preferably used in combination while aligning the fiber direction, but they may be used alone respectively.

<Place for Locating Elastic Sheet>

As shown in FIG. 11, since the shape of female labium minus pudendi is thicker and longer in the forward portion compared with the backward portion, the inter-labia pressure is higher and the fluctuation of the inter-labia pressure is also greater in the forward portion. In FIG. 11, the direction A shows the forward direction of the labia and the direction B shows the backward direction of the labia. Accordingly, it is also preferred to control the compressibility and the bulk recoverability between the forward portion and the backward portion. That is, it is preferably constituted such that the compression ratio and the bulk recoverability are higher in the forward portion than those in the backward portion.

Further, as shown in FIG. 12 and FIG. 13, the elastic sheet 650 may be disposed only in the forward portion. FIG. 12 is a cross sectional view along line $X_1$-$X_2$ in FIG. 11, that is, for the forward labial portion, while FIG. 13 is a cross sectional view along line $Y_1$-$Y_2$ in FIG. 11, that is, for the backward labial portion. As can be seen from FIG. 12 and FIG. 13, the elastic sheet 650 is disposed only at the forward portion of the inter-labial pad 600 (FIG. 12) and the elastic sheet 650 is not disposed in the backward portion thereof.

Figure 14:
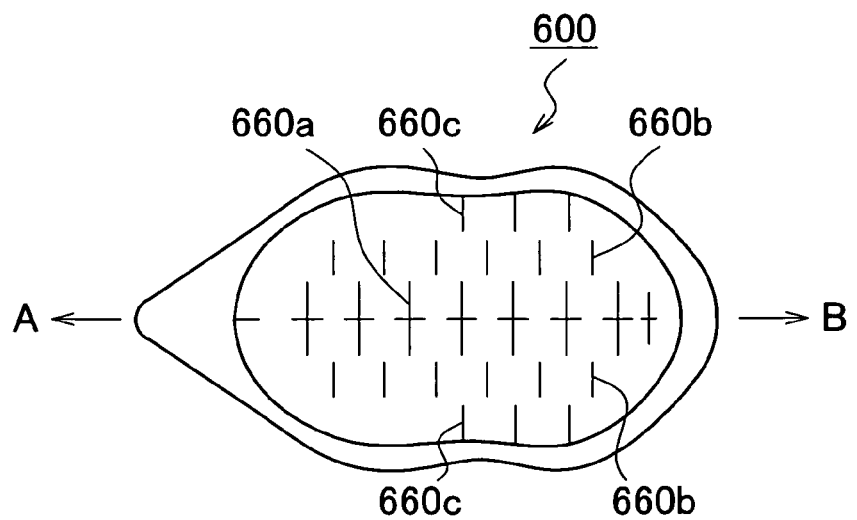
FIG. 14 is an upper view showing a modified example of the inter-labial pad according to the fifth embodiment of the invention.

Further, one or plural slits may also be disposed along the shorter direction of the inter-labial pad 600 from the forward to the backward portions. Thus, since the external pressure applied strongly to the forward portion of the inter-labial pad 600 is separated by the slit portions, the external pressure is less propagated backward of the inter-labial pad. Specifically, as shown in FIG. 14, for example, it is preferred that perforated slits 660a, 660b and 660c are formed in a zigzag slit pattern such that the slit length is from 5 to 20 mm along the longitudinal direction of the inter-labial pad 600, and the slit pitch is from 5 to 20 mm along the longitudinal direction of the inter-labial pad 600. The direction A shows the forward direction of the labia while the direction B shows the backward direction of the labia.

<Example of Surface Side Sheet>

For the surface side sheet 620, those materials which are water permeable and give less stimulations to skins are used. They include, for example, those non-woven fabrics obtained by a manufacturing method such as a point bonding or through air method, which are used alone or in a composite form. Among the materials, those mainly comprising at least hydrophilic cellulosic fibers are preferred in view of the affinity with the inter-labial inner walls so that deviation is not caused between the inter-labial pad and the labial inner wall to give a foreign-body sensation to a wearer. Specifically, spun laced non-woven fabrics obtained by mixing from 5 to 30% of natural cotton and from 70 to 95% of rayon or acetate, conditioning to a range from 20 to 50 $g/m^2$, then entangling fibers to each other by water jet entanglement followed by drying and conditioning the thickness within a range from 0.3 to 1.0 mm are preferred. The thread material used in this case is selected materials having a fiber denier of within a range from 1.1 to 6.6 dtex and a fiber length from a range of 15 to 60 mm for natural cotton and from a range of 25 to 51 mm for rayon or acetate. Further, they may be also films having perforated apertures or fiber layers laminated with films and having perforated apertures.

<Example of Back Face Sheet>

As the back face sheet 630, any material capable of preventing menstrual blood kept in the absorbent body 610 from leaking to the outside of the inter-labial pad may be used. Further, by the use of moisture permeable materials, steaming during wearing can be decreased and uncomfortable feeling during wearing can be reduced. The materials of the less water permeable sheet include polyethylene, polypropylene, polyethylene terephthalate, polyvinyl alcohol, polylactic acid, polybutyl succinate, non-woven fabric, paper and laminate materials thereof at a thickness from 15 to 60 μm. Further, the materials may also be an air permeable film obtained by filling inorganic fillers and applying stretching. Specifically, they include films mainly comprising low density polyethylene resin and conditioned within a range of basis weight per unit area of from 15 to 30 $g/m^2$, and further, air permeable films controlled within a range of an open pore area percentage of from 10 to 30% and an aperture diameter of from 0.1 to 0.6 mm. Example of the non-woven fabrics include spun bonded non-woven fabric, point bonded non-woven fabric, and through air non-woven fabric, etc. which may be applied with a water repelling treatment. Among them, SMS (spun bond/melt-blown/spun bond) non-woven fabrics containing melt-blown fibers constituted with ultrafine fibers and with extremely small inter-fiber distance are preferred. In this case, it is preferred to constitute within the range of basis weight per unit area of from 5 to 15 $g/m^2$ for the spun bonded layer, from 1 to 10 $g/m^2$ for the melt-blown layer and from 5 to 15 $g/m^2$ for the spun bonded layer.

<Example for Bonding Absorbent Body and Surface Side and Back Face Sheets>

As the specific method for bonding the absorbent body and the surface side sheet and the back face sheet, known-techniques such as adhesives or embossing seal can be used. The adhesive coating pattern includes, for example, spiral coating, controlled seam coating, coater coating, curtain coater coating and summit gun coating. Among them, the summit gun coating capable of making the pitch finer between bonded portion and non-bonded portion is preferred. The basis weight per unit area of the adhesive is within a range from 1 to 30 $g/m^2$, preferably, from 3 to 10 $g/m^2$. Further, in a pattern where the adhesive is coated linearly, the line width is preferably within a range from 30 to 300 μm. In a case where the basis weight is 1 $g/m^2$ or less, or the line width is less than 30 μm, when the surface side sheet 620 is constituted with a fiber aggregate, the adhesive is buried between the fibers failing to provide a sufficient bonding force. On the other hand, in a case where the basis weight per unit area is more than 30 $g/m^2$ or the line width is more than 300 μm, the peripheral portion becomes rigid. There is no particular restriction for the portion coated with the adhesive and it is preferred that the adhesive is coated at least between the absorbent body and the back face sheet.

The emboss pattern may be a lattice-shape, dot-shape, corrugated shape, etc. with no particular restriction. The location for emboss sealing also has no particular restriction and it is preferred that emboss sealing is applied for the surface side sheet and the back face sheet extending along the peripheral edge of the absorbent body together.

<Example of a State of Wearing and a Shape of Inter-Labial Pad>

While the depth of the labia is different depending on the individual since it is about 14 mm as an average value, a region put between the labia is in a region within 14 mm from the vestibular floor in the vertical direction attached to the labia. Further, in an inter-labial pad in which the shape changes before and after attachment in the labia, for example, an inter-labial pad folded along the longitudinal center line as an axis of fold such that the portions of the back face sheet are opposed to each other during wearing, the region is within 14 mm in both outward directions from the longitudinal center line respectively. Further, the region put between the labia along the longitudinal direction is 50 mm forward and 5 mm backward to the ostium vaginae since the length of the labia is generally 55 mm as the average value. Accordingly, the region put longitudinally between the labia is a region within 50 mm for the forward and within 5 mm for the backward from the position in contact with the ostium vaginae.

The shape of the inter-labial pad is not particularly limited so long as it is a shape that conforms the female labia such as elliptic shape, hour glass shape or droplet shape. The total size for the outer profile is preferably from 40 to 180 mm and, more preferably, 80 to 120 mm in the longitudinal direction. Further, it is preferably from 20 to 100 mm and, more preferably, from 50 to 80 mm in the lateral direction. The inter-labial pad may be contained entirely in the labia or may have a region exposing out of the labia.

<Individual Wrapping Container for Inter-Labial Pad>

The inter-labial pad according to the invention is preferably contained further in an individual wrapping container. The materials for the individual wrapping container include polyethylene, polypropylene, polyethylene terephthalate, polyvinyl alcohol, polylactic acid, polybutyl succinate, non-woven fabric, and paper, as well as laminate materials thereof, at a thickness of from 15 to 60 µm. Specifically, they include films, formed by mixing low density polyethylene ranging from 0 to 80% and high density polyethylene ranging from 100 to 20% and controlling the basis weight per unit area within a range from 15 to 35 $g/m^2$. Further, films applied with stretching for improving the resin orientation may also be used. Examples of non-woven fabrics include spun bonded non-woven fabrics, point bonded non-woven fabrics, and through air non-woven fabrics, which may be applied with a water repelling treatment. Among them, SMS non-wove fabrics containing melt-blown fibers constituted with ultrafine fibers with extremely small inter-fiber distance are preferred. In this case, it is preferred that they are constituted with the basis weight per unit area within a range from 5 to 15 $g/m^2$ for a spun bonded layer, from 1 to 10 $g/m^2$ for a melt-blown layer and from 5 to 15 $g/m^2$ for a spun bonded layer. Further, it is preferred that the individual wrapping container can shield the color of the menstrual blood absorbed in the inter-labial pad and may be mixed with a pigment in a range from 0.2 to 10%, or applied with printing on the surface, for example, with an ink. Further, the inter-labial pad or the individual wrapping container may comprise a water disintegratable material or biodegradable material so that the pad can be flushed away.

[Compressibility and Bulk Recoverability]

The compressibility and the bulk recoverability in the present invention can be estimated by the following method. At first, predetermined compressibility and bulk recoverability in the present invention are preferably the compressibility and the bulk recoverability in a moistened state of absorbing a body fluid.

As an evaluation method for the compressibility in the moistened state of absorbing the body fluid, the thickness of the inter-labial pad after pressurization at 50 $g/cm^2$ for 3 min in a state where the inter-labial pad absorbs an artificial body fluid seven times as much as the mass of the absorbent body is measured and the ratio relative to the thickness of the inter-labial pad before absorption of the artificial body fluid is measured. This is defined as a compression ratio. In the inter-labial pad according to the invention, the compression ratio is, preferably, 30% or more and, more preferably, 30% or more and 80% or less.

As an evaluation method for the bulk recoverability in the moistened state of absorbing the body fluid, the thickness of the inter-labial pad after pressurization at 50 $g/cm^2$ for 3 min and further leaving under no pressure for 2 min in a state where the inter-labial pad absorbs an artificial body fluid seven times as much as the mass of the absorbent body is measured and the ratio relative to the thickness of the inter-labial pad before absorption of the artificial body fluid is measured. This is defined as a bulk recovery ratio. In the inter-labial pad according to the present invention, the bulk recovery ratio is preferably 60% or more and, more preferably, 60% or more and 150% or less.

The artificial body fluid used for the evaluation described above includes an artificial menstrual blood prepared as follows. An example of specific composition in a case of using the artificial menstrual blood includes, for example, a solution of a composition comprising 32 mass parts of sodium carboxymethyl cellulose, 320 mass parts of glycerin, 40 mass parts of sodium chloride, 16 mass parts of sodium hydrogen carbonate, 32 mass parts of food pigment preparation Red No. 102, 8 mass parts of food pigment preparation Red No. 2, and 8 mass parts of food pigment preparation Yellow No. 5, with no restriction thereto.

EXAMPLE

The present invention is to be described more specifically with reference to examples and comparative examples. The compressibility and bulk recoverability in the present invention concern not only the absorbent body but also the entire inter-labial pad. However, in the following examples and comparative examples, the values for the compressibility and bulk recoverability of the entire inter-labial pad after releasing compression were measured only for the absorbent body. This is because most of the factors giving an influence on such physical values are attributable to those of the absorbent body occupying a major portion of the weight for the entire inter-labial pad.

Example 1

Using 100% of pulp with a fiber length of 1 to 8 mm, as shown in FIG. 4, fibers were fiber-opened by an air laid method using a garnet type fiber opening method while increasing the collection speed relative to the conveying speed, amending them by suction such that the basis weight per unit area was 700 $g/m^2$, conveying them so as not to apply excess tension during the conveying step and then applying embossing at an embossing ratio of 0.5% with a dot-shape emboss pattern, to manufacture an absorbent body.

The lamination conditions were at an attraction pressure under suction of 7000 Pa, at a conveying speed of 80 m/min, and at an emboss roll circumferential speed/conveyor belt circumferential speed of 1.2. Further, in the dot-shape emboss roll, pins each of 1.0 mm diameter are arranged in a dot-pattern (1.0 mm diameter means a diameter at the pin tip and the diameter at the pin bottom was 2.6 mm) at a pitch of 12.5 mm and arranged in a zigzag manner.

Example 2

An absorbent body was manufactured under the same conditions as those in Example 1 except for using fibers formed by mixing 85% of rayon with a fiber denier of 3.3 dtex having a fiber length of 51 mm, fiber crimping ratio of 50%, and deposited with 0.2% of a hydrophilic oil agent, and 15% of natural cotton.

Example 3

Using 100% synthetic fibers of PE-PP core-sheath eccentric type with a fiber denier of 4.4 dtex having a fiber length of 51 mm, fiber crimping ratio of 60% and deposited with a hydrophilic oil agent of 0.2%, the synthetic fibers were sheeted into a non-woven fabric of 20 $g/m^2$ by a through air method, the non-woven fabric was stacked by 35 sheets so as to be 700 g/m² and then embossing was applied in the same manner as in Example 1.

Example 4

(a) Using the same 100% synthetic fibers as in Example 3, the synthetic fibers were fiber-opened by an air laid method using a garnet type fiber opening method while increasing the collection speed relative to the conveying speed, and they were collected by suction such that the basis weight per unit area was 100 g/m² as shown in FIG. 4. (b) On the other hand, a non-woven fabric formed by sheeting the synthetic fibers described above by a through air manufacturing method into 20 g/m² was stacked by 13 sheets so as to be 260 g/m². (a) was placed over (b) and the same embossing as in Example 1 was applied. Then, it was folded with the central axis as the start point.

As the lamination conditions, the suction pressure was set to 4,000 Pa and other conditions were set in the same manner as in Example 1.

Comparative Example 1

Articles, trade name of: "Envive" manufactured by Procter & gamble Co. in the prior art described above were used as they were.

Test Example

Compression ratio and bulk recovery ratio were measured for the absorbent bodies of Examples 1 to 4 and Comparative Example 1. Table 1 shows the results. The measurement for the compression ratio and the bulk recovery ratio were evaluated in accordance with the test method as described in [Compressibility and bulk recoverability] and, as an artificial menstrual blood, a solution of a composition comprising 32 mass parts of sodium carboxymethyl cellulose, 320 mass parts of glycerin, 40 mass parts of sodium chloride, 16 mass parts of sodium hydrogen carbonate, 32 mass parts of food pigment preparation Red No. 102, 8 mass parts of food pigment preparation Red No. 2 and 8 mass parts of food pigment preparation Yellow No. 5 was used.

TABLE 1

| | No. | | Comparative Example 1 | Example 1 | Example 2 | Example 3 | Example 4 |
|---|---|---|---|---|---|---|---|
| Sample | Upper layer | Manufacturing method | envive | Fiber opening lamination | Fiber opening lamination | Through air stocked by 35 sheets of 20 g/m² | Fiber opening lamination |
| | | Raw material | | 100% - Pulp → fiber length of 1-8 mm | 85% - Rayon → fiber denier of 4.4 dt × fiber length of 51 mm 15%-Natural cotton | PE-PP core-eccentric type fiber: 100% → fiber denier of 4.4 dt × fiber length of 51 mm | PE-PP core-eccentric type fiber: 100% → fiber denier of 4.4 dt × fiber length of 51 mm |
| | | Basis weight per unit area | | | | | 100 g/m² |
| | Lower layer | Manufacturing method Raw material | | | | | Through air stacked by 13 sheets of 20 g/m² PE-PP core-eccentric type fiber: 100% → fiber denier of 4.4 dt × fiber length of 51 mm |
| | | Basis weight per unit area | | | | | 260 g/m² |
| | Settled total basis weight per unit area | g/m² | | 700 | 700 | 700 | 360 |
| | Processing | | | Dot-shape emboss | Dot-shape emboss | Dot-shape emboss | Dot-shape emboss |
| | Shape putted to labia | | Two-folded | Rectangular shape | Rectangular shape | Rectangular shape | Two-folded |
| Dry | Weight | g | 1.02 | 1.02 | 1.01 | 1.24 | 1.19 |
| | <1> Thickness → 6.1 g/cm² or less | mm | 5.98 | 6.52 | 6.8 | 8.48 | 9.21 |
| | Density | g/cm³ | 0.085 | 0.104 | 0.099 | 0.097 | 0.086 |
| Wet → Absorption magnification: 7 fold | <2> Thickness upon compression → 50 g/cm² or less | mm | 2.97 | 3.36 | 3.65 | 4.43 | 4.19 |
| | Thickness after releasing of compression → 6.1 g/cm² or less | mm | 3.52 | 3.98 | 4.58 | 6.72 | 7.81 |
| | <3>/<1> × 100 Recovery ratio | % | 59 | 61 | 67 | 79 | 85 |
| | (<1> − <2>)/<1> × 100 Compression ratio | % | 50 | 48 | 46 | 48 | 55 |

From the result of Table 1, the bulk recovery ratio was 61% and the volume after releasing compression was 3.98 mm in Example 1, and the bulk recovery ratio was 67% and the volume after releasing the compression was 4.58 mm in Example 2, all of the values were higher compared with the bulk recovery ratio of 59% and the volume of 3.52 mm after releasing the compression in Comparative Example 1. This is because, in Comparative Example 1, since the direction of the fibers of the absorbent body was aligned in front-to-back direction, in a state where pressure was added and menstrual blood was absorbed, other fibers were further intruded between fibers to shorten the distance between the fibers, and this reduced the thickness of the absorbent body to result in lowering of bulk recoverability.

On the other hand, in Example 1 and Example 2, since the fiber orientation was partially directed to the direction of the thickness upon collection, the bulk recoverability was increased by the rigidity of the fibers. Further, the values in Example 2 were higher than those in Example 1, this is because, since the fiber length was longer than that in Example 1, other fibers were less intruded between fibers.

In Example 3, the bulk recovery ratio was 79% and the bulk after releasing compression was 6.72 mm. It is considered that since the fibers were crimped synthetic fibers, the fiber rigidity was scarcely lowered and the fiber tended to recover the original shape even in a moistened state and, in addition, the embossed portions were press-bonded by heating, and the fiber orientation directing to the direction of the thickness was more firm. In addition, since the sheet per se was a through air non-woven fabric being melted by heat at entangling points between each of fibers, the bulk recovery ratio was high even in a more moistened state.

In Example 4, the compression ratio was 55% and the bulk recovery ratio was 85%. The compression ratio was high because the fibers at the upper layer were bonded only at embossed portions and, accordingly, the degree of freedom of the fibers with each other was high, which gave less foreign-body sensation to a wearer. In addition, it is considered that the bulk recovery ratio was higher than that in Example 2 because repulsive force tending to return to the original shape was applied due to folding at the center axis.

The present invention can be used as an inter-labial pad which is put at a portion thereof between the female labial space and abutting it at the inner surface of the labia in wearing.

What is claimed is:

1. An inter-labial pad for absorbing a body fluid and for inserting between the labia of a user, comprising:
    a surface side sheet;
    a back face sheet; and
    an absorbent body having a forward labial portion and a backward labial portion along a longitudinal axis, the absorbent body being disposed between the surface side sheet and the back face sheet, said absorbent body including a pressure recoverable structure having a preferred compressibility and a bulk recoverability and responding to an inter-labial pressure placed on the inter-labial pad from the right and left sides of the labia when worn, said pressure recoverable structure including an elastic sheet member which is selected from groups of laminates of elastic fibers, films, and foamed materials having air cells, the elastic sheet member further being in contact with the back face sheet and being disposed at the first end portion of the absorbent body and terminating prior to the second end portion of the absorbent body opposed from the first end portion;
    wherein the inter-labial pad has a substantially longitudinal shape having a longitudinal direction and a lateral direction and is folded such that a pair of portions of the back face sheet are opposed to each other along a longitudinal crease of the inter-labial pad, and wherein a pair of portions of the at least one elastic sheet member are opposed to each other and each portion of the pair of portions of the at least one elastic sheet member is in contact with a respective one of the pair of portions of the back face sheet; and
    wherein each portion of the at least one elastic sheet member is disposed between the back face sheet and the absorbent body, and the absorbent body prevents each portion of the at least one elastic sheet member from contacting the surface side sheet.

2. The inter-labial pad according to claim 1, wherein the absorbent body comprises absorbing fibers for absorbing the body fluid, and the pressure recoverable structure is formed by orienting at least a portion of the absorbing fibers constituting the absorbent body in the right-to-left direction.

3. The inter-labial pad according to claim 1, wherein the pressure recoverable structure is disposed symmetrically with the longitudinal crease of the inter-labial pad as an axis of symmetry.

4. The inter-labial pad according to claim 1, wherein the absorbent body comprises absorbing fibers for absorbing the body fluid and the absorbing fibers constituting the absorbent body are crimped fibers.

5. The inter-labial pad according to claim 1, wherein the absorbent body comprises absorbing fibers for absorbing the body fluid and at least a portion of the absorbing fibers constituting the absorbent body is synthetic fibers.

6. The inter-labial pad according to claim 1, wherein the predetermined compressibility and bulk recoverability are higher in a forward portion of the inter-labial pad situating at the front of a wearer than in a backward portion of the inter-labial pad situated at the back of the wearer.

7. The inter-labial pad according to claim 6, wherein the inter-labial pad is provided with one or more slits from the forward portion to the backward portion.

8. The inter-labial pad according to claim 1, wherein the preferred compressibility and bulk recoverability are provided in a moistened state of absorbing the body fluid.

9. The inter-labial pad according to claim 1, wherein the inter-labial pad, after it has absorbed body fluid about seven times as much as the mass of the absorbent body, provide (a) a compression ratio in which the thickness of the inter-labial pad after it has been pressed at a pressure of 50 g/cm$^2$ for 3 min is 30% or more relative to the thickness of the inter-labial pad before it absorbs the artificial body fluid, and (b) a bulk recovery ratio in which the thickness of the inter-labial pad after it has been pressed at the pressure of 50 g/cm$^2$ for 3 min, and, further, left under no pressure for 2 min is 60% or more relative to the thickness of the inter-labial pad before it absorbs the artificial body fluid.

10. The inter-labial pad according to claim 9, wherein the compression ratio is 30% or more and 80% or less, and the bulk recovery ratio is 60% or more and 150% or less.

11. The inter-labial pad according to claim 1, wherein the thickness of the inter-labial pad before it absorbs the artificial body fluid is from 3 mm to 10 mm and, the thickness of the inter-labial pad after it has been pressed at a pressure of 50 g/cm$^2$ for 3 min and further left under no pressure for 2 min in a state where it has absorbed a body fluid about seven times as much as the mass of the absorbent body is 3.8 mm or more and 15 mm or less.

12. The inter-labial pad according to claim 1, wherein a compressibility and bulk recoverability of the absorbent body including the at least one pressure recoverable structure are higher in the forward labial portion of the absorbent body than in the backward labial portion of the absorbent body.

13. The inter-labial pad according to claim 1, wherein each portion of the at least one elastic sheet member is disposed vertically centered between the longitudinal crease and bottom fold of the interlabial pad.

14. An inter-labial pad for absorbing a body fluid and for inserting between the labia of a user, comprising:

a surface side sheet;

a back face sheet; and an absorbent body having a first end portion and a second end portion along a longitudinal axis, the absorbent body being disposed between the surface side sheet and the back face sheet, said absorbent body including a pressure recoverable structure having predetermined compressibility and bulk recoverability and responding to an inter-labial pressure placed on the inter-labial pad from the right and left sides of the labia when worn, said pressure recoverable structure including an elastic sheet member which is a laminate of elastic fibers, the elastic sheet member further being in contact with the back face sheet and being disposed at the first end portion of the absorbent body and terminating prior to the second end portion of the absorbent body opposed from the first end portion;

wherein the inter-labial pad has a substantially longitudinal shape having a longitudinal direction and a lateral direction and is folded such that a pair of portions of the back face sheet are opposed to each other along a longitudinal crease of the inter-labial pad, and wherein a pair of portions of the at least one elastic sheet member are opposed to each other and each portion of the pair of portions of the at least one elastic sheet member is in contact with a respective one of the pair of portions of the back face sheet; and wherein each portion of the at least one elastic sheet member is disposed between the back face sheet and the absorbent body, and the absorbent body prevents each portion of the at least one elastic sheet member from contacting the surface side sheet.

\* \* \* \* \*